(12) United States Patent
Schoisswohl et al.

(10) Patent No.: US 6,966,878 B2
(45) Date of Patent: Nov. 22, 2005

(54) METHOD AND APPARATUS FOR OBTAINING A VOLUMETRIC SCAN OF A PERIODICALLY MOVING OBJECT

(75) Inventors: Armin Schoisswohl, Wels (AT); Peter Falkensammer, Völklabruck (AT)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 105 days.

(21) Appl. No.: 10/650,264

(22) Filed: Aug. 28, 2003

(65) Prior Publication Data

US 2005/0049503 A1    Mar. 3, 2005

(51) Int. Cl.$^7$ .............................................. A61B 8/00
(52) U.S. Cl. ...................................... 600/443; 128/916
(58) Field of Search ............................... 600/443, 447, 600/500–502, 513; 126/916

(56) References Cited

U.S. PATENT DOCUMENTS

| | | | | |
|---|---|---|---|---|
| 5,099,847 | A | * | 3/1992 | Powers et al. ............... 600/443 |
| 5,159,931 | A | | 11/1992 | Pini |
| 5,570,430 | A | * | 10/1996 | Sheehan et al. ............ 382/128 |
| 5,976,088 | A | * | 11/1999 | Urbano et al. .............. 600/443 |
| 6,139,500 | A | * | 10/2000 | Clark .......................... 600/443 |
| 6,190,321 | B1 | * | 2/2001 | Pang et al. .................. 600/441 |
| 6,450,962 | B1 | | 9/2002 | Brandl et al. |
| 6,647,135 | B2 | * | 11/2003 | Bonnefous .................. 382/128 |

OTHER PUBLICATIONS

S.Brekke, E. Tegnander, H. Torp and S.H. Eik-Nes, Dynamic 3D ultrasonic imaging of the fetal heart, 2002 IEEE Ultrasonic Symposium.

Thomas R. Nelson, PhD, Dolores H. Pretorius, MD, Mark Sklansky, MD, Sandra Hagen-Ansert, BA, Three-Dimensional Echocardiographic Evaluation of Fetal Heart Anatomy and Function; Acquistion, Analysis and Display, 1996 by the American Institute of Ultrasound in Medicine, J Ultrasound Med 15:1-9, 1996, 0279-4297/96/$3.50.

Mark Skylansky, MD, Thomas R. Nelson, PhD, Dolores H. Pretorius, MD, Three-Dimensional Fetal Echocardiography: Gated Versus Nongated Techniques, 1998 by the American Institute of Ultrasound in Medicine, J Ultrasound Med 17:451-467, 1998, 0278-4297/98/$3.50.

Mark Sklansky, MD, Thomas Nelson, PhD, Monet Strachan, RDCS, Dolores Pretorius, MD, Real-Time Three-Dimensional Fetal Echocardiography: Initial Feasibility Study, 1999 by the American Institute of Ultrasound in Medicine, J Ultrasound Med 18:745-752, 1999, 0278-4297/99/$3.50.

* cited by examiner

Primary Examiner—Francis J. Jaworski
(74) Attorney, Agent, or Firm—Pete Vogel, Esq.; Armstrong Teasdale LLP

(57) ABSTRACT

Method and apparatus for acquiring and processing a volumetric scan of a periodically moving object. A volumetric scan is performed of the periodically moving object which repeats a cycle of movement over time. A time interval of the periodic movement of the object is identified within the volumetric scan, and the volumetric scan is rearranged based on the time interval.

23 Claims, 8 Drawing Sheets

US 6,966,878 B2

1

METHOD AND APPARATUS FOR OBTAINING A VOLUMETRIC SCAN OF A PERIODICALLY MOVING OBJECT

BACKGROUND OF THE INVENTION

This invention relates generally to diagnostic ultrasound systems. In particular, the present invention relates to method and apparatus for obtaining a volumetric scan of a periodically moving object within a body.

A current challenge exists to perform a multidimensional ultrasound scan of a quickly, and more or less rhythmically, moving object within a body, such as a fetal heart. Currently, volume probes having a conventional one-dimensional (1D) array, which is mechanically moved in the elevation direction, as well as electronically steered 2D arrays, may be used for the acquisition. This technique makes it possible to acquire pyramid-shaped volume data sets. To image the fetal heart, high frame rate acquisitions are necessary, no matter whether 2D or 3D data sets are being acquired. For acquiring 3D data sets in real-time, one limitation is the constant speed of sound at 1540 m/s; this limits the amount of data to be acquired per second and thus these acquisitions are a tradeoff between frame rate and image quality. To acquire and achieve high frame rates, the line density has to be decreased, which significantly impairs lateral and elevation resolution.

One approach is to perform ECG-triggered volumetric acquisitions as described in U.S. Pat. No. 5,159,931 to Pini, Nov. 3, 1992, which is hereby incorporated by reference in its entirety, which works well when imaging the adult heart, but is generally not available for the fetal heart due to absence of an appropriate fetal ECG signal. Alternatively, one may acquire data of several heart cycles at several fixed positions which are recorded with a position sensor, and obtain cardiac motion information via Fourier transform methods as described in Nelson et al, "Three Dimensional Echocardiographic Evaluation of Fetal Heart Anatomy and Function: Acquisition, Analysis, and Display", J Ultrasound Med 15:1–9, 1996, which is hereby incorporated by reference in its entirety. Another problem is experienced when imaging a fetal heart during early pregnancy with 2D fetal echocardiography, when the relationship between fetus and amniotic fluid allows a lot of movement. If the fetus is very active, it may be time consuming or impossible at the time of the scheduled exam to acquire sufficient cardiac data.

Thus, a system and method are desired to obtain multidimensional data sets of a quickly moving object within a body that addresses the problems noted above and others previously experienced.

BRIEF DESCRIPTION OF THE INVENTION

In one embodiment, a method of processing a volumetric scan of a periodically moving object comprises performing a volumetric scan of a periodically moving object. A time interval of a periodic movement of the object is identified within the volumetric scan, and the volumetric scan is rearranged based on the time interval.

In one embodiment, a method of acquiring a diagnostic image of a periodically moving object comprises acquiring a series of scan planes. The series of scan planes comprise a moving object which repeats a cycle of movement over time, and the series of scan planes are acquired over at least two movement cycles. At least one common point of interest is identified within each of the series of scan planes. Intensity values of the common points of interest are compared between the series of scan planes. At least two intensity values are identified based on a result of the comparison, and the series of scan planes are rearranged based on the intensity values.

In one embodiment, an apparatus for acquiring a volumetric scan of a periodically moving object comprises a transducer having an array of elements for transmitting and receiving ultrasound signals to and from an area of interest. The area of interest comprises a periodically moving object. A transmitter drives the array of elements to scan the periodically moving object once in a single direction. A receiver receives the ultrasound signals which comprise a series of adjacent scan planes. A memory stores the series of adjacent scan planes as a volumetric data set, and a processor processes the series of adjacent scan planes. The processor identifies a time interval based on the periodically moving object, and rearranges the series of adjacent scan planes based on the time interval.

DETAILED DESCRIPTION OF THE INVENTION

Figure 1:
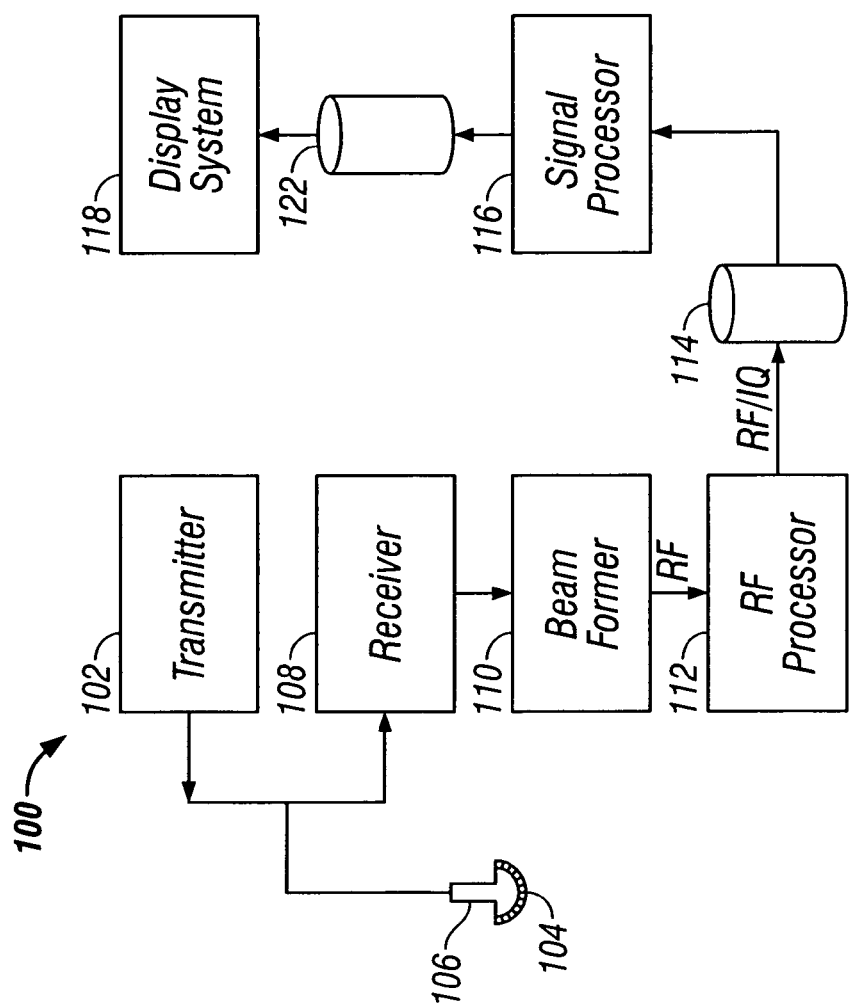
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives an array of elements 104 within a transducer 106 to emit pulsed ultrasonic signals into a body. A variety of geometries may be used. The ultrasonic signals are back-scattered from structures in the body, like blood cells or muscular tissue, to produce echoes which return to the elements 104. The echoes are received by a receiver 108. The received echoes are passed through a beamformer 110, which performs beamforming and outputs an RF signal. The RF signal then passes through an RE processor 112. Alternatively, the RF processor 112 may include a complex demodulator (not shown) that demodulates the RE signal to form IQ data pairs representative of the echo signals. The RE or IQ signal data may then be routed directly to RF/IQ buffer 114 for temporary storage.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Therefore, the signal processor 116 may be used to perform the functions of a STIC analyzer and converter 42 and a volume display processor 46, which are described below. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation. An image buffer 122 is included for storing processed frames of acquired ultrasound information that are not scheduled to be displayed immediately. The image buffer 122 may comprise any known data storage medium.

Figure 2:
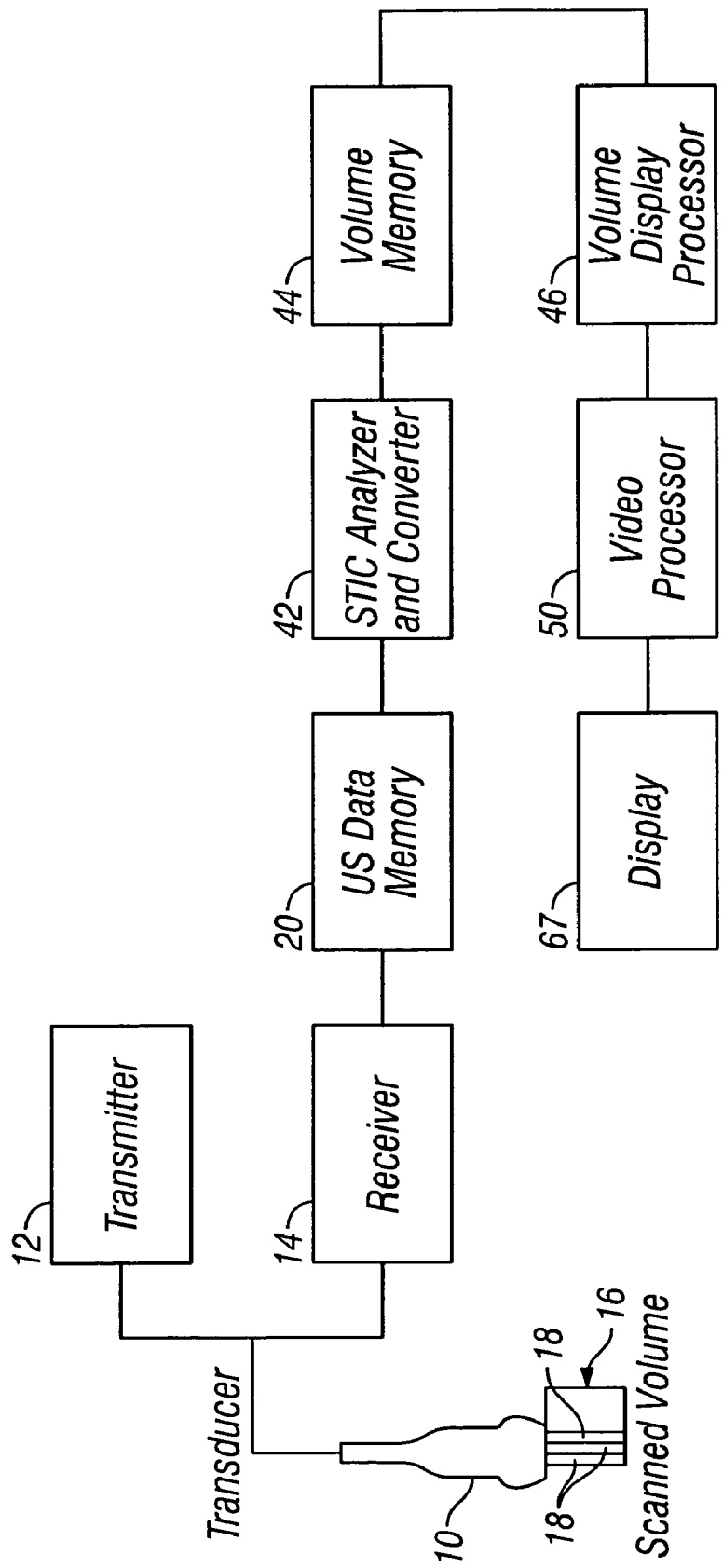
FIG. 2 illustrates an ultrasound system formed in accordance with an embodiment of the present invention.

FIG. 2 illustrates an ultrasound system formed in accordance with one embodiment of the present invention. The system includes a transducer 10 connected to a transmitter 12 and a receiver 14. The transducer 10 transmits ultrasonic pulses and receives echoes from structures inside of a scanned ultrasound volume 16. Memory 20 stores ultrasound data from the receiver 14 derived from the scanned ultrasound volume 16. The volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains scan planes 18. The scan planes 18 are stored in the memory 20, and then passed to a spatial and temporal image correlation (STIC) analyzer and converter 42. In some embodiments, the transducer 10 may obtain lines instead of the scan planes 18, and the memory 20 may store lines obtained by the transducer 10 rather than the scan planes 18. Data output by the STIC analyzer and converter 42 is stored in volume memory 44 and is accessed by a volume display processor 46. The volume display processor 46 performs volume rendering and/or other image processing techniques upon the data. The output of the volume display processor 46 is passed to the video processor 50 and display 67.

The position of each echo signal sample (Voxel) is defined in terms of geometrical accuracy (i.e., the distance from one Voxel to the next), ultrasonic response, and derived values from the ultrasonic response. Suitable ultrasonic responses may include B-flow, gray scale values, color flow values, and angio or power Doppler information.

Figure 3:
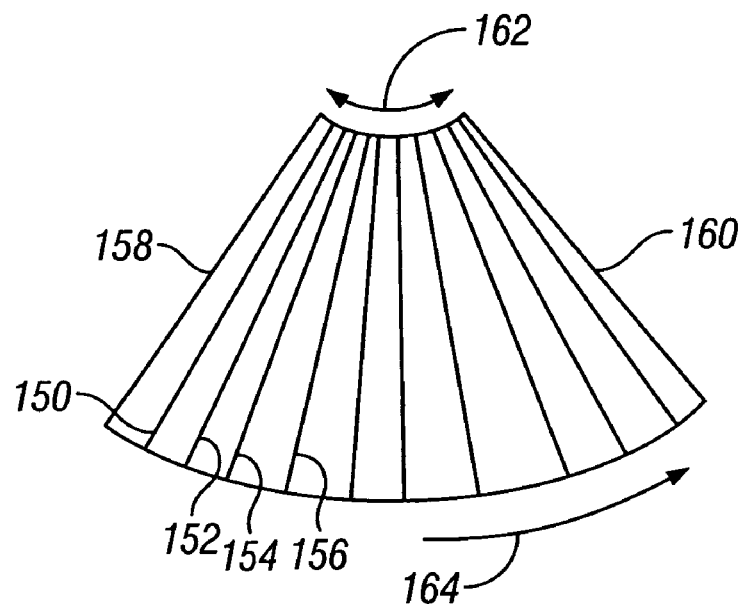
FIG. 3 illustrates a series of projecting scan planes acquired by the ultrasound system of FIGS. 1 and/or 2 in accordance with an embodiment of the present invention.

FIG. 3 illustrates a series of projecting scan planes acquired by the ultrasound system 100 of FIGS. 1 and/or 2. Each line 150-156 represents a scan plane into the page, and the elevation 164 of the scan is indicated. Although FIG. 3 illustrates the scan planes in a fan-shape, it should be understood that the fan-shape is not a limitation, and that other shapes, such as a rectangle with parallel scan planes, for example, may also be acquired. The following discussion will be based on acquiring data representing the fetal heart, but it should be understood that other periodically moving objects may be similarly scanned and processed, such as an adult heart, a heart valve, an artery, a vein and the like. Also, although the modality discussed is ultrasound, the image acquisition and processing techniques may be used with other modalities, such as CT, MRI, and the like.

Similarly, the information acquired by the ultrasound system 100 is not limited to B-mode information only, but may also contain information gathered from evaluating several lines from the same sample volume (e.g., color Doppler, power Doppler, tissue Doppler, B-flow, Coded Excitation, harmonic imaging, and the like). These data of different ultrasound modalities or scanning techniques may also be acquired simultaneously, and may be used either for analysis, display, or both.

The transducer 10 is held in one position throughout the acquisition, and is positioned to acquire data representative of the item of interest, such as the fetal heart. The elements 104, or array of elements 104, are electronically or mechanically focussed to direct ultrasound firings longitudinally to scan along adjacent scan planes, and external position sensing is not necessary.

A single, slow, acquisition sweep acquiring adjacent scan planes 18 may start, by way of example only, at border 158, and end at border 160. Other start and end points of the acquisition sweep may also be used. By way of example only, the acquisition sweep may have a sweep angle 162 of 20 degrees and a time period including several, or at least two, movement cycles of the fetal heart. Other sweep angles 162 may be used. The acquisition sweep may be accomplished by continuously moving the focus of the ultrasound firings or by changing the focus in small increments.

Alternatively, the acquisition sweep may have an acquisition time period covering multiple movement cycles, and the sweep angle 162 may be changed to reflect the type and/or size of anatomy being scanned. An acquisition with a longer acquisition time will acquire more data and the spatial resolution will be better when compared to a scan acquired over a shorter acquisition time. An acquisition with a higher frame rate will result in better temporal resolution than a scan acquired with a lower frame rate. The elements 104 are focussed to acquire the adjacent scan planes 18 very close to each other spatially.

Each scan plane represented by the lines 150–156 in FIG. 3 is a 2D image having a resolution in time. By way of example only, if the resolution in time is within a range of 50–150 Hz, 50–150 scan planes, respectively, may be acquired for every 2 degrees of sweep angle 162, for an acquisition time of 10 seconds and a sweep angle 162 of 20 degrees. The resolution in time is not limited by this example. For clarity, not all of the scan planes are illustrated.

Figure 13:
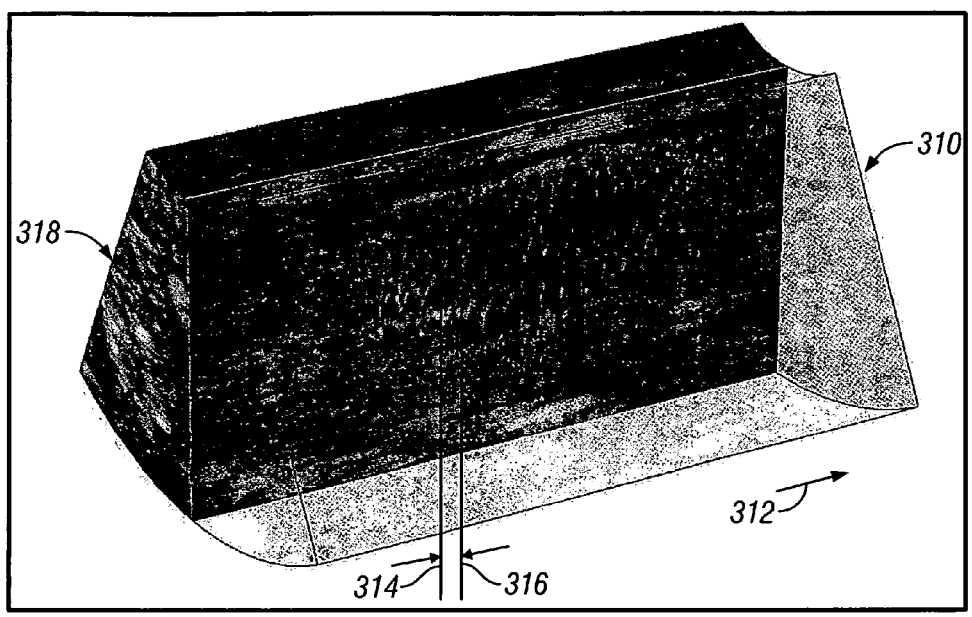
FIG. 13 illustrates a series of scan planes of a fetal heart in accordance with an embodiment of the present invention.

FIG. 13 illustrates a series of scan planes 310 of a fetal heart. The beating of the fetal heart during the acquisition causes a rhythmical pattern of changes in the diameter of the heart. The scan planes are acquired in the combined direction of space and time 312. Markers 314 and 316 are included to illustrate the fetal heart rate. Calculating the fetal heart rate is discussed below.

Figure 4:
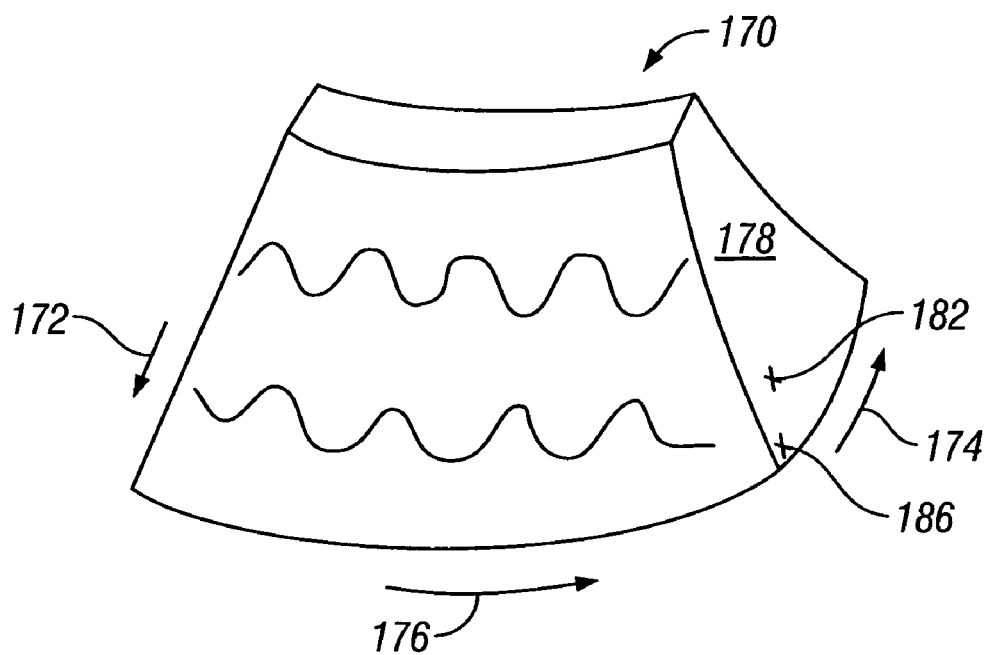
FIG. 4 illustrates a series of adjacent scan planes acquired in accordance with an embodiment of the present invention.

FIG. 4 illustrates a series of adjacent scan planes 170, such as the adjacent scan planes acquired in FIG. 3. The scan planes are illustrated over combined space and time 176 with axial 172 and azimuth 174 directions as indicated.

Therefore, the elevation is orthogonal to the scan planes 170. A 2D image 178 having data indicative of one scan plane of the fetal heart is represented at the end of the adjacent scan planes 170. Referring again to FIG. 13, 2D image 318 also comprises data of one scan plane of the fetal heart.

Figure 5:
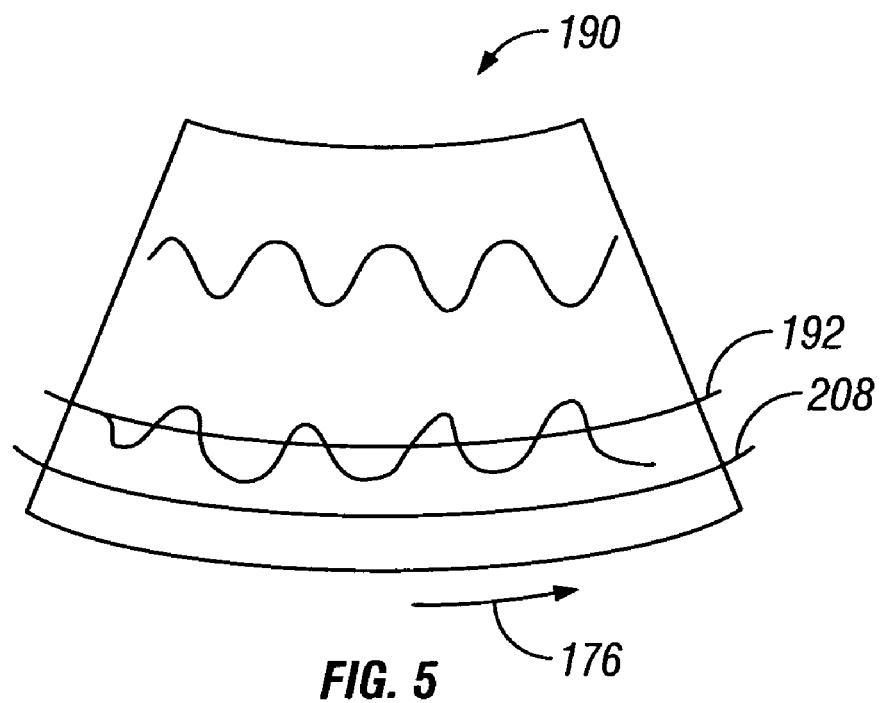
FIG. 5 illustrates a 2D slice of the adjacent scan planes of FIG. 4 in accordance with an embodiment of the present invention.

FIG. 5 illustrates a 2D slice 190 of the adjacent scan planes 170 of FIG. 4. An image correlation technique is used to extract the movement of the fetal heart from the scan plane data.

Returning to FIG. 4, the signal processor 116 chooses an x,y coordinate, point 182, from image acquisition system coordinates. By way of example only, the coordinates may be polar, rectangular, and the like, and are not limited to a specific acquisition geometry. The point 182 is identified on each scan plane. In FIG. 5, line 192 is illustrated. Line 192 corresponds to points 182, and therefore runs through the series of adjacent scan planes 170 at the same x,y coordinate.

Figure 6:
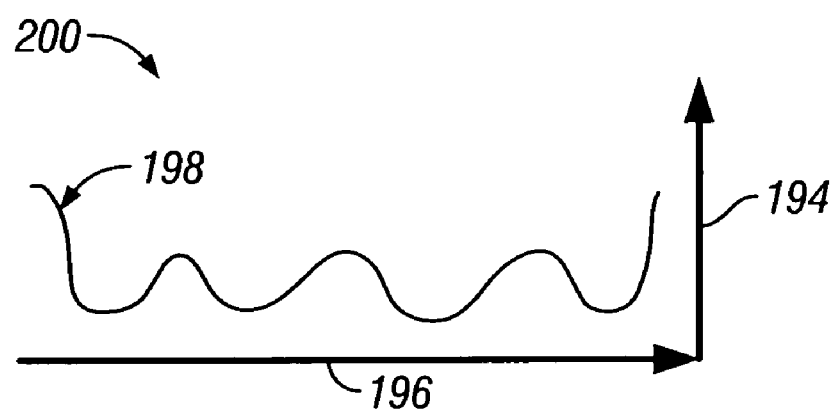
FIG. 6 illustrates a plot of intensity over time and space for an x,y point in accordance with an embodiment of the present invention.

FIG. 6 illustrates a plot 200 of intensity 194 over time and space 196 for the point 182. Therefore, an intensity value is identified for the point 182 on each image frame and displayed over time as intensity line 198. The periodic movement of the fetal heart introduces periodic intensity variation (as illustrated by the rhythmical pattern of the intensity line 198). The variations in intensity are analyzed by the STIC analyzer and converter 42 in order to obtain movement information. It should be understood that the plot 200 is a representation only, and that other methods, such as storing the identified intensity values in memory 20, volume memory 44, or image buffer 122 may be used.

Figure 7:
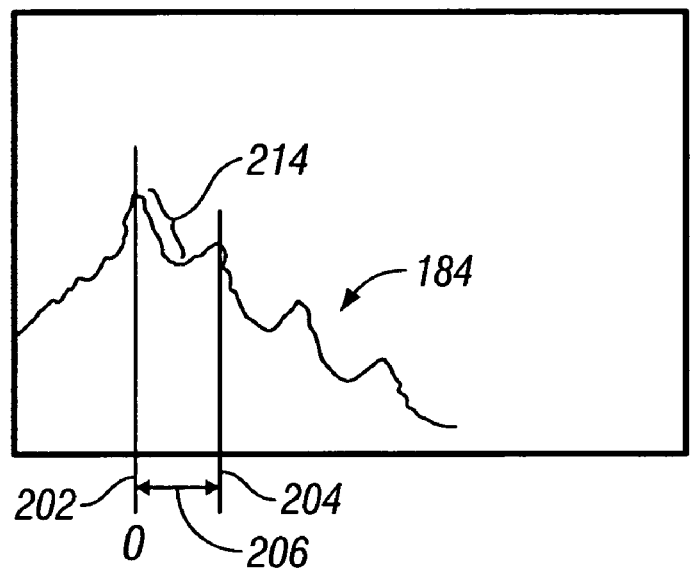
FIG. 7 illustrates an autocorrelation of an intensity line of an x,y point in accordance with an embodiment of the present invention.

FIG. 7 illustrates an autocorrelation 184 of intensity line 198. The autocorrelation 184 may be calculated by the STIC analyzer and converter 42 by taking the autocorrelation function of the intensity line 198, such as by using the following equation:

$$A(y) = \int s(x) \cdot \overline{s(x-y)} dx$$

wherein A(y) is the autocorrelation function of the signal s, x is the integration variable in the spatio-temporal domain, y is the lag of the autocorrelation function, and s is the intensity line 198.

By calculating the autocorrelation 184, a peak 202 at a zero-position is identified. The peak 202 is the highest peak, or the peak with the most energy. The STIC analyzer and converter 42 then identifies a first significant local maximum 204, which is the peak with the next highest energy. The STIC analyzer and converter 42 calculates a time interval 206 between the peak 202 and the first significant local maximum 204. The time interval 206 identifies the period of the heart cycle. Once the time interval 206 is known, the STIC analyzer and converter 42 determines how many adjacent scan planes were acquired within the time interval 206.

Alternatively, the heart cycle may be calculated using Fast Fourier Transform Analysis (FFT). The STIC analyzer and converter 42 or signal processor 116 may identify the frequency of the movement as the location of the first significant local maximum 204 in a power spectrum of the intensity line 198. In addition, Doppler methods may be used to determine the velocity of tissue movement to identify specific motion states (e.g., Systole, diastole, etc) of the object.

Figure 8:
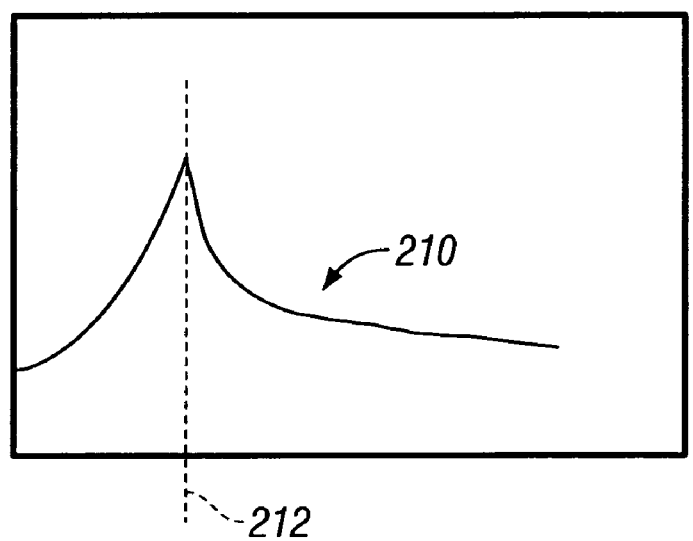
FIG. 8 illustrates an autocorrelation of an intensity line of an x,y point in accordance with an embodiment of the present invention.

FIG. 8 illustrates an autocorrelation 210 of intensity line 208 (FIG. 5). The autocorrelation function was taken of the intensity line 208, which corresponds to a point 186 (FIG. 4) identified outside the heart. Therefore, there is little or no periodic movement, and intensity line 208 may only have one significant peak 212. A time interval cannot be calculated.

Figure 9:
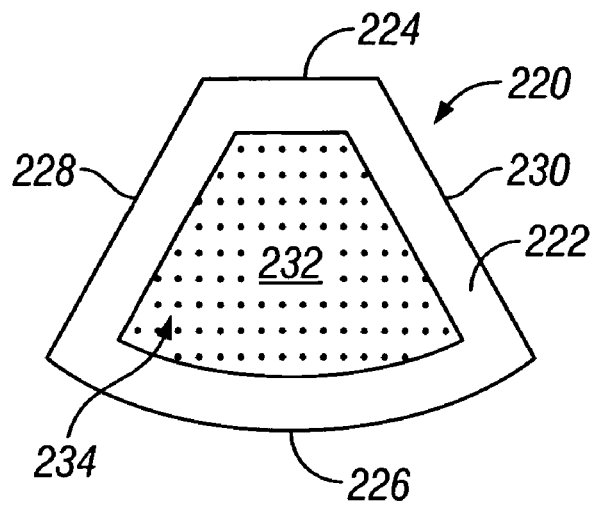
FIG. 9 illustrates a single 2D image in accordance with an embodiment of the present invention.

FIG. 9 illustrates a single 2D image 220 similar to the 2D image 178 of FIG. 4. For simplicity, it may be assumed that the heart or other moving object of interest is approximately in the center of the 2D image 220. Therefore, the signal processor defines a border 222 around an interior portion 232 of the 2D image 220. The border 222 may be a predefined number of pixels in from the top 224, bottom 226 and sides 228, 230 towards the interior portion 232 of the 2D image 220. The border 222 need not be symmetrical along all edges.

The STIC analyzer and converter 42 defines a number of points 234 (similar to points 182 and 186 of FIG. 4) within the interior portion 232. The number of points 234 may be defined by a pattern having a defined size and resolution. For example, the pattern may resemble a chess board in which every other point is chosen. Alternatively, every $4^{th}$ or $10^{th}$ point may be chosen. The pattern may change based upon user preference, or upon the anatomy being scanned. For example, a different template may be offered for a fetal heart, heart valve, artery, and the like. Optionally, the STIC analyzer and converter 42 may randomly select a predefined number of points 234 within the interior portion 232. The number of points 234 and/or the size and resolution of the pattern may vary depending upon factors such as processing speed, image resolution, and the like.

Returning to FIG. 5, a line (similar to lines 192 and 208) is defined for each point in the number of points 234 (FIG. 9). An intensity line 198 (FIG. 6), or intensity values, are defined for each of the lines corresponding to the number of points 234. The autocorrelation 184 is then taken of each intensity line 198.

It should be understood that although FIG. 9 represents a 2D image, the above method may be applied to data acquired using other acquisition modes, such as Doppler, B-flow, and the like.

Figure 10:
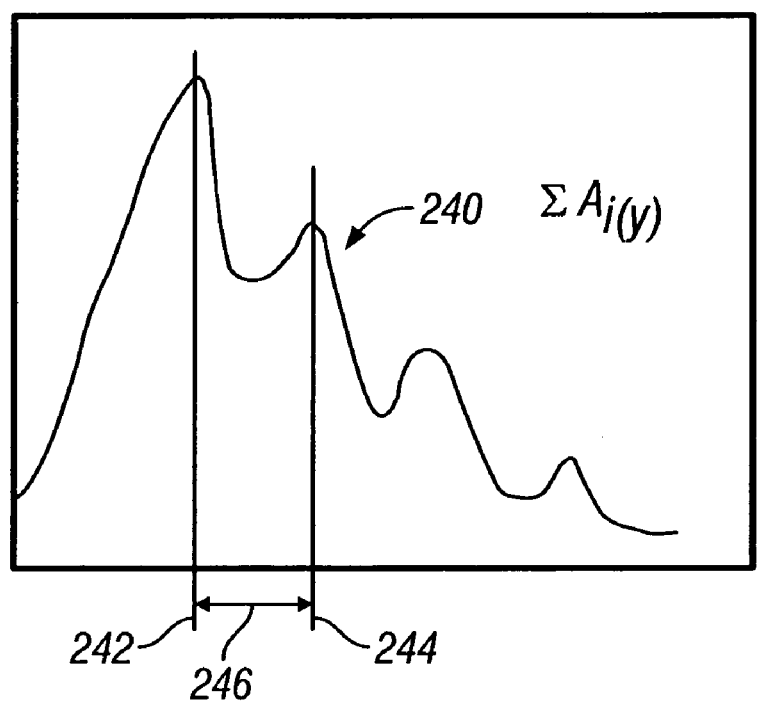
FIG. 10 illustrates a summed autocorrelation in accordance with an embodiment of the present invention.

FIG. 10 illustrates a summed autocorrelation 240. The STIC analyzer and converter 42 sums the autocorrelations taken for each point in the number of points 234. By summing the autocorrelations, noise 214 (FIG. 7) is effectively removed from the summed autocorrelation 240. In addition, points located in areas not experiencing movement, such as above or below the heart (point 186) do not prevent the STIC analyzer and converter 42 from calculating the average time interval 246. Alternatively, a filter or windowing function may be used in addition to remove noise 214.

The STIC analyzer and converter 42 identifies a peak 242 at zero (having the highest intensity) and a first significant local maximum 244 as discussed previously. The time interval calculated between the zero peak 242 and the first significant local maximum 244 is the average time interval 246 of one movement cycle. The STIC analyzer and converter 42 now determines the number of scan planes occurring within the average time interval 246, or heart cycle.

Figure 11:
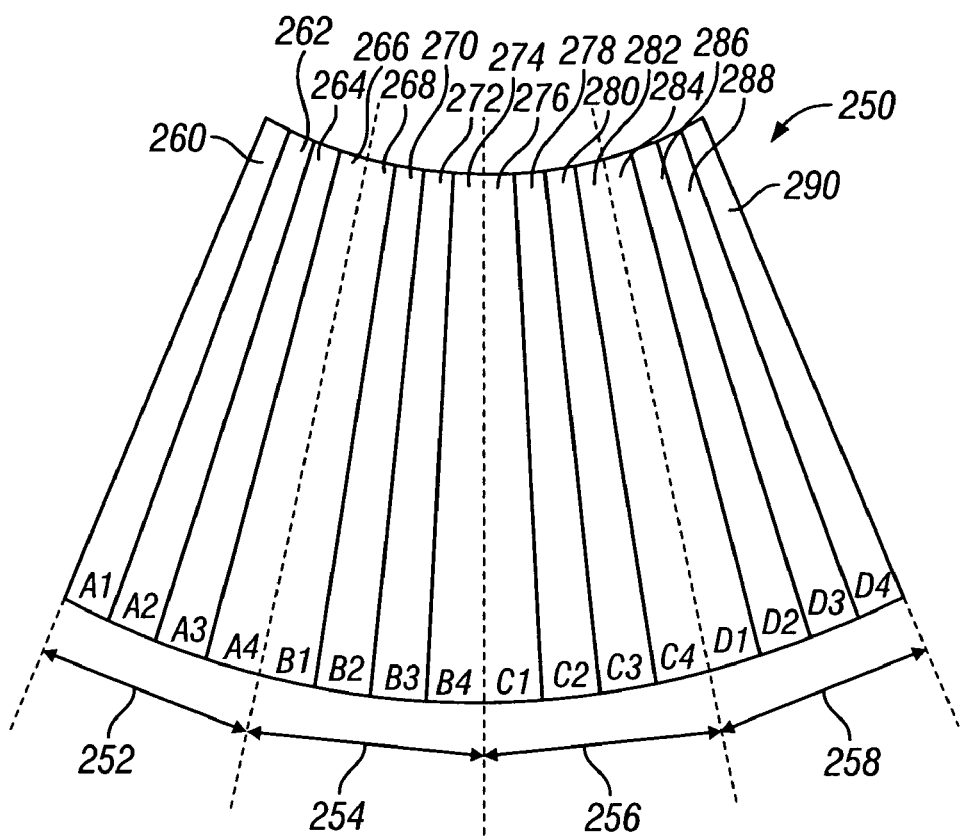
FIG. 11 illustrates a series of adjacent scan planes acquired in accordance with an embodiment of the present invention.

FIG. 11 illustrates a series of adjacent scan planes 250 similar to the adjacent scan planes 170 of FIG. 4. Time intervals 252–258 separate the series of adjacent scan planes 250 into the number of slices determined by the STIC analyzer and converter 42. The location of time intervals 252–258 within the series of adjacent scan planes 250 need not correspond to the start and end of the heart cycle. Therefore, the STIC analyzer and converter 42 may choose any scan plane within the series of adjacent scan planes 250 to begin sectioning the data into time intervals 252–258. The STIC analyzer and converter 42 may move forward and backward through the series of adjacent scan planes 250 to section the data into the time intervals 252–258. By way of example only, the series of adjacent scan planes 250 comprise 4 scan planes within each time interval 252–258. Time interval 252 comprises scan planes 260–266, time interval 254 comprises scan planes 268–274, time interval 256 comprises scan planes 276–282, and time interval 258 comprises scan planes 284–290. When imaging a fetal heart or other anatomy as discussed previously, however, many more scan planes would be acquired within each time interval 252–258.

The STIC analyzer and converter 42 rearranges the order of the scan planes 260–290 and combines the scan planes acquired at the same phase, or point in time within the heart cycle, but from a different lateral position, into a volume. As illustrated in FIG. 11, scan planes A1 260, B1 268, C1 276, and D1 284 were acquired during the same phase within the heart cycle. Similarly, each of the following subsets of scan planes [scan planes A2 262, B2 270, C2 278, D2 286], [scan planes A3 264, B3 272, C3 280, D3 288], and [scan planes A4 266, B4 274, C4 282, D4 290] were acquired during the same phase within the heart cycle.

Figure 12:
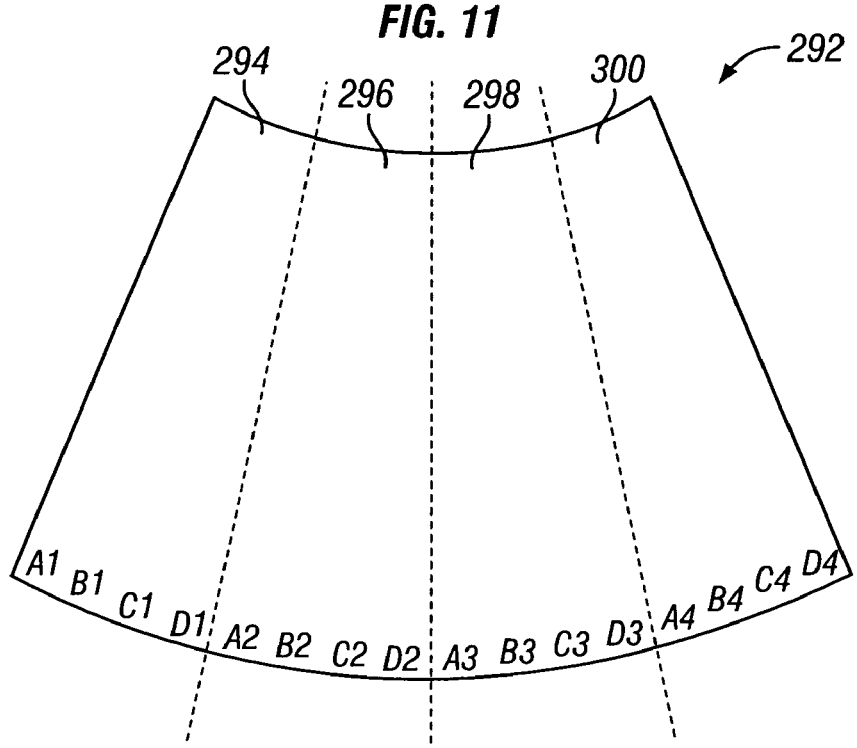
FIG. 12 illustrates a series of volumes corresponding to the subsets of scan planes of FIG. 11 in accordance with an embodiment of the present invention.

FIG. 12 illustrates a series of volumes 292 corresponding to the subsets of scan planes 260–290 of FIG. 11. While the volume 250 of FIG. 11 incorporates two purely spatial dimensions and one combined spatio-temporal dimension, each of the volumes 294–300 of FIG. 12 has purely 3 spatial dimensions and covers data from a single point in time (relative to the heart cycle).

The STIC analyzer and converter 42 combines each subset of scan planes 260–290 into one volume. Therefore, volume 1 294 comprises the image data of scan planes A1 260, B1 268, C1 276, and D1 284. Volume 2 296 comprises the image data of scan planes A2 262, B2 270, C2 278, and D2 286. Volume 3 298 comprises the image data of scan planes A3 264, B3 272, C3 280, and D3 288. Volume 4 comprises the image data of scan planes A4 266, B4 274, C4 282, and D4 290. Each volume 294–300 comprises a snapshot of the fetal heart during one single beat.

The series of volumes 292 may be displayed in three orthogonal planes in a cycle, such as a cineloop, which allows a user to navigate through the volumes 294–300 and view individual volumes. When imaging a fetal heart, for example, approximately 40–60 volumes 294–300 may be created and displayed on display 67. Each of the 40–60 volumes 294–300 represents a fixed point within the heart cycle.

Alternatively, the data may be processed and displayed in other ways. For example, the volume display processor 46 may render the image data to show the inner 3D structure of the heart. For example, maximum intensity projection, minimum intensity projection, average projection, and the like may be calculated and displayed. Also, a single volume 294–300, or a portion or slice of a volume 294–300, may be selected for display. The selected portion may be rotated on the display 67 or further processed separate from the remaining volume data. In addition, an anatomic M-mode image representing a single selected point within the volumes may be displayed over time. The heart rate and/or other data may also be displayed.

Now that the series of volumes 292 has been created, it may be stored in a memory, such as ultrasound data memory 20, image buffer 122, a hard drive, a floppy, CD, or DVD drive, or on a server on a network. The series of volumes 292 and/or the unprocessed volumetric data may also be transferred via a network or one of the aforementioned portable discs to be further processed and reviewed at a different location after the patient has left the examination. Having the data available to be reviewed and processed later is advantageous, especially during early pregnancy, when the relationship between fetus and amniotic fluid allows a lot of movement. Once the data is acquired, fetal movement is no longer an issue, as previously discussed in relation to 2D fetal echocardiography.

While the invention has been described in terms of various specific embodiments, those skilled in the art will recognize that the invention can be practiced with modification within the spirit and scope of the claims.

What is claimed is:

1. A method of processing a volumetric scan of a periodically moving object, comprising:
    performing a volumetric scan of a periodically moving object;
    identifying a time interval of a periodic movement of said periodically moving object within said volumetric scan based on movement information determined from scan data acquired by the volumetric scan; and
    rearranging said volumetric scan based on said time interval.

2. The method of claim 1, said volumetric scan further comprising adjacent scan planes, said method further comprising:
    identifying a quantity of adjacent scan planes within said time interval;
    dividing said adjacent scan planes based on said time interval; and
    combining scan planes having a same point in time with respect to said time interval.

3. The method of claim 1, said volumetric scan further comprising two dimensions of spatial information and one dimension of combined spatio-temporal information.

4. The method of claim 1, said volumetric scan being performed using one of color flow, power Doppler, tissue Doppler, B-flow, and B-mode.

5. The method of claim 1, said performing step further comprising scanning said periodically moving object once in a single direction.

6. The method of claim 1, said volumetric scan further comprising adjacent scan planes, said method further comprising:
    dividing said adjacent scan planes into subsets based on said time interval;
    identifying a point in time for each scan plane within said subsets with respect to said time interval; and
    combining said scan planes having a same point in time into volumes, said volumes comprising three spatial dimensions.

7. The method of claim 1, said performing step further comprising scanning said periodically moving object once in a single direction over at least two time intervals.

8. A method of acquiring a diagnostic image of a periodically moving object, comprising:
    acquiring a series of scan planes corresponding to a moving object, said moving object repeating a cycle of movement over time, said acquiring being accomplished over at least two movement cycles;
    identifying at least one common coordinate point of interest within each of said series of scan planes;
    comparing intensity values of said at least one common coordinate point of interest between said series of scan planes;
    identifying at least two intensity values within said series of scan planes based on a result of said comparing step; and rearranging said series of scan planes based on said at least two intensity values.

9. The method of claim 8, said comparing step further comprising calculating an autocorrelation of said intensity values of said at least one common point.

10. The method of claim 8, further comprising calculating a time interval between said at least two intensity values, said time interval identifying a length of said cycle of movement.

11. The method of claim 8, said identifying at least one common point step further comprising:
   identifying border areas of said series of scan planes around an interior portion, a size of said border areas being predefined; and
   said at least one common point being defined within said interior portion based on a pattern, said pattern having a size and resolution based on at least one of a speed of said moving object, a size of said moving object, and a template corresponding to an anatomy of said moving object.

12. The method of claim 8, said at least one common point further comprising between every two points and every 10 points of said series of scan planes.

13. The method of claim 8, further comprising:
   identifying at least one additional common point of interest within each of said series of scan planes;
   calculating autocorrelations of said intensity values of said at least one common point and said at least one additional common point; and
   calculating a sum of said autocorrelations, said rearranging step being based on said sum.

14. The method of claim 8, further comprising:
   calculating a time interval between said at least two intensity values, said time interval identifying a length of said cycle of movement over time;
   identifying a number of said series of scan planes within said time interval; and
   combining at least two scan planes into a volume, said scan planes having a same position in time with respect to said time interval.

15. The method of claim 8, further comprising:
   storing said series of scan planes in a memory; and
   retrieving said series of scan planes from said memory prior to said identifying at least one common point step.

16. The method of claim 8, said acquiring step further comprising scanning said moving object once in a single direction.

17. The method of claim 8, wherein said at least two intensity values being maximum values.

18. An apparatus for acquiring a volumetric scan of a periodically moving object, comprising:
   a transducer comprising an array of elements for transmitting and receiving ultrasound signals to and from an area of interest comprising a periodically moving object;
   a transmitter for driving said array of elements to scan said periodically moving object once in a single direction;
   a receiver for receiving said ultrasound signals, said ultrasound signals comprising a series of adjacent scan planes;
   a memory for storing said series of adjacent scan planes as a volumetric data set; and
   a processor for processing said series of adjacent scan planes, said processor identifying a time interval based on said periodically moving object based on movement information determined from said series of adjacent scan planes, said processor rearranging said series of adjacent scan planes based on said time interval.

19. The apparatus of claim 18, said moving object comprising one of a fetal heart, a heart, a heart valve, a vein, and an artery.

20. The apparatus of claim 18, said processor further comprising:
   identifying at least one common point on each said scan plane;
   identifying intensity values of said at least one common point; and
   determining at least two peak intensity values, said time interval being based on said at least two peak intensity values.

21. The apparatus of claim 18, said processor further comprising:
   identifying multiple common points of interest on each said scan plane;
   identifying intensity values for each of said multiple common points;
   calculating autocorrelations of said intensity values; and
   calculating an average of said autocorrelations, said time interval being based on said average.

22. The apparatus of claim 18, said processor further comprising:
   identifying multiple common points of interest on each said scan plane;
   identifying intensity values of said multiple common points;
   calculating a power spectrum of said intensity values; and
   identifying said time interval based on a zero point and a first significant local maximum in said power spectrum.

23. The apparatus of claim 18, said processor further comprising combining scan planes having a same position within said time interval into a series of volumes.

* * * * *